United States Patent [19]

Lok et al.

[11] 4,451,557
[45] May 29, 1984

[54] PHOTOGRAPHIC SPEED INCREASING AND LATENT IMAGE STABILIZING COMPOUNDS, SILVER HALIDE EMULSIONS, AND PHOTOGRAPHIC ELEMENTS

[75] Inventors: Roger Lok, Hilton; John P. Freeman, Rochester; William N. Baum, Henrietta, all of N.Y.

[73] Assignee: Eastman Kodak Company, Rochester, N.Y.

[21] Appl. No.: 466,244

[22] Filed: Feb. 14, 1983

Related U.S. Application Data

[63] Continuation-in-part of Ser. No. 320,794, Nov. 12, 1981, Pat. No. 4,378,426.

[51] Int. Cl.$^3$ .................... G03C 1/46; G03C 1/06
[52] U.S. Cl. .................... 430/505; 430/551; 430/600; 430/614
[58] Field of Search ............... 430/614, 600, 505, 542, 430/543, 551

[56] References Cited

U.S. PATENT DOCUMENTS

| | | | |
|---|---|---|---|
| 3,764,339 | 10/1973 | Himmelmann et al. | 430/614 |
| 3,910,791 | 10/1975 | vonKonig et al. | |
| 3,954,478 | 5/1976 | Arai et al. | |
| 4,115,122 | 9/1978 | Adachi et al. | |
| 4,256,830 | 3/1981 | Jager et al. | |
| 4,277,557 | 7/1981 | Jager et al. | 430/614 |
| 4,374,196 | 2/1983 | Herz | 430/505 |
| 4,378,426 | 3/1983 | Lok et al. | 430/505 |

OTHER PUBLICATIONS

Herz U.S. Ser. No. 236,360, filed Feb. 20, 1981.
Kuwabara and Iwai, "Effects of Acetyleneic Derivatives on Photographic Emulsions," *Bulletin of the Soc. of Scientific Phot. of Japan*, No. 16, Dec. 1966, pp. 14–23.

*Primary Examiner*—J. Travis Brown
*Attorney, Agent, or Firm*—Carl O. Thomas

[57] ABSTRACT

Photographic silver halide emulsions show increased speed and reduced latent image fading when a compound of the following structure is incorporated:

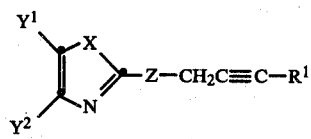

wherein:
X is —O—, —S—, —Se—, or

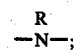

$Y^1$ and $Y^2$ individually represent hydrogen or an aromatic nucleus or together represent the atoms completing a fused aromatic nucleus;
Z is

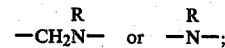

R is hydrogen or lower alkyl of from 1 to 5 carbon atoms; and
$R^1$ is hydrogen or methyl.

16 Claims, No Drawings

PHOTOGRAPHIC SPEED INCREASING AND LATENT IMAGE STABILIZING COMPOUNDS, SILVER HALIDE EMULSIONS, AND PHOTOGRAPHIC ELEMENTS

This is a continuation-in-part of U.S. Ser. No. 320,794, filed Nov. 12, 1981, now U.S. Pat. No. 4,378,426.

FIELD OF THE INVENTION

This invention relates to novel compounds capable of increasing photographic speed and reducing latent image fading when incorporated in photographic silver halide emulsions, to the photographic emulsions in which they are incorporated, and to photographic elements containing the emulsions.

BACKGROUND

A visible image is formed in silver halide photographic materials by exposure of the material to actinic radiation to form a record of the exposure which is invisible to the unaided eye, followed by processing of the material to yield a visible image.

The visible record of exposure is referred to as a latent image. It is generally agreed that the latent image comprises minute specks of metallic silver formed in or on individual silver halide grains by interaction between silver ions and photoelectrons generated by absorption of actinic radiation by the silver halide grains.

Processing of most common silver halide photographic materials includes a development step in which the material is contacted with an aqueous alkaline solution of a developing agent. The developing agent is a reducing agent which will selectively reduce to metallic silver those silver halide grains containing a latent image.

It is known that the latent image is not permanent and that, with the passage of time, silver halide grains which would be developable immediately after exposure become nondevelopable. This phenomenon is termed latent image fading and manifests itself as a loss in image density in the developed image and a consequent loss in speed in the silver halide photographic material.

If silver halide materials were developed immediately following imagewise exposure, latent image fading would not be a problem. However, with many silver halide materials delays between exposure and processing frequently occur. For example, with amateur film materials in which multiple images are formed on a single roll of film there is often a delay of months between the time the first image is exposed and the time the exposed roll of film is sent for processing. With such materials latent image fading can present a significant problem and compounds are added to photographic materials to prevent or reduce it. These compounds are referred to as latent image stabilizing compounds or latent image stabilizers and the prevention or reduction of latent image fading is referred to as latent image stabilization.

Among latent image stabilizers known in the art are N-2-propenylbenzothiazolium and naphthothiazolium salts described in Arai et al U.S. Pat. No. 3,954,478. N-2-Propenyl substituent containing acyclic compounds useful as latent image stabilizers are disclosed in Herz U.S. Ser. No. 236,360, filed Feb. 20, 1981, SILVER HALIDE EMULSIONS CONTAINING LATENT IMAGE STABILIZING COMPOUNDS, now U.S. Pat. No. 4,374,196. Latent image stabilizers containing a 2-propynylthio substituent are disclosed by von Konig et al U.S. Pat. No. 3,910,791.

Prior to this present invention there has existed in the art a bias against incorporating compounds containing an 2-propynylamino group into silver halide emulsions as addenda. Kuwabara and Iwai, "Effects of Acetylenic Derivatives on Photographic Emulsions," *Bulletin of the Society of Scientific Photography of Japan*, No. 16, December 1966, pp. 14–23, reports that compounds containing a 2-propynylamino group—i.e., 2-propargylamine and its substituted derivatives—produced fog in negative-working silver halide emulsions. On the other hand, if the 2-propynyl group is attached to a nitrogen atom of an unsaturated ring, fog was not produced (with one exception). Jager et al U.S. Pat. No. 4,256,830 reports the effectiveness of certain 2-propynyl group containing compounds against color fog and reduced contrast, but in all instances of the 2-propynyl group attached to a nitrogen atom, the nitrogen atom is part of a ring. Adachi et al U.S. Pat. No. 4,115,122 discloses certain 2-propynyl substituted heterocyclic compounds to be useful as nucleating agents. In variant forms the 2-propynyl group is attached to the heterocyclic ring through an oxy linkage. In no instance is the 2-propynyl group attached to the heterocyclic ring through an amine linkage.

The various 2-propenyl and 2-propynyl groups identified can be alkyl substituted in most instances—i.e., include corresponding 2-butenyl and 2-butynyl substituents.

DESCRIPTION OF PREFERRED EMBODIMENTS

In one aspect this invention is directed to a compound represented by the formula:

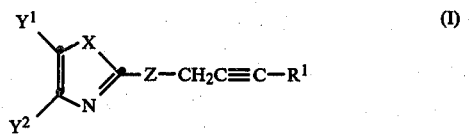

(I)

wherein:

X is —O—, —S—, —Se—, or

$Y^1$ and $Y^2$ individually represent hydrogen or an aromatic nucleus or together represent the atoms completing a fused aromatic nucleus;

Z is

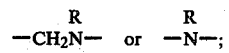

R is hydrogen or lower alkyl of from 1 to 5 carbon atoms; and $R^1$ is hydrogen or methyl, provided that $Y^1$ and $Y^2$ individually represent hydrogen or an aromatic nucleus when $R^1$ is hydrogen. (When $R^1$ is hydrogen and $Y^1$ and $Y^2$ together represent the atoms completing a fused aromatic ring, this is the specific subject matter of U.S. Ser. No. 320,794, cited above.)

In another aspect this invention is directed to a photographic silver halide emulsion containing a photographically effective amount of a compound according to formula (I).

In still another aspect this invention is directed to a photographic element comprised of a support and, located thereon, at least one layer comprised of a photographic silver halide emulsion as described above.

In an additional aspect this invention is directed to incorporating in a silver halide emulsion in a photographically effective amount a compound according to formula (I).

It has been discovered that 2-propynylamino and 2-butynylamino substituted compounds, as indicated above are useful both in reducing latent image fading and in increasing photographic sensitivity. This discovery is surprising, since the art has previously taught that 2-propynylamino and 2-butynylamino substituents to heterocyclic nuclei produce fog in photographic silver halide emulsions. The photographic effectiveness of the compounds of this invention is even more surprising, since our own investigations have revealed analogues of the compounds of this invention wherein Z is an oxy (—O—) linkage to be strongly desensitizing compounds.

In the above formula $Y^1$ and $Y^2$ individually represent hydrogen or an aromatic nucleus, such as phenyl or naphthyl, or together represent the atoms completing a fused aromatic nucleus, such as the atoms completing benzo or naphtho aromatic rings fused with the indicated heterocyclic ring.

In a preferred form of the invention the 2-propynylamino and 2-butynylamino substituent is attached to a benzoxazole, benzothiazole, benzoselenazole, or benzimidazole heterocyclic nucleus. In one specific preferred form the compounds of the present invention can be represented by the following formula:

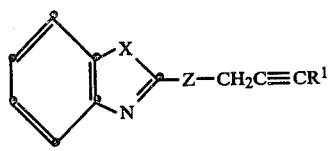

(II)

In each of formula (I) and (II) Z is a divalent methylamino linking group, $$-CH_2\overset{R}{N}-,$$

or a divalent amino linking group $$-\overset{R}{N}-.$$

R can be hydrogen or lower alkyl of from 1 to 5 carbon atoms, including methyl, ethyl, n-propyl, iso-propyl, n-butyl, iso-butyl, tert-butyl, n-pentyl, iso-pentyl, 3-pentyl, and neo-pentyl. In a specifically preferred form R is hydrogen or methyl. When the heterocyclic nucleus is a benzimidazole nucleus and R thus occurs twice in formulae (I) and (II), R can be independently selected in each occurrence.

Preparation of varied compounds satisfying formulae (I) and (II) is apparent from the exemplary compound preparations described below. In general, a heterocyclic compound corresponding to the desired heterocyclic nucleus and containing a halo substituent at the desired reactive site is reacted with 2-propynylamine or a-butynylamine.

Specific preferred 2-propynylamino and 2-butynylamino substituted heterocycles satisfying formulae (I) and (II) are set forth in Table I.

TABLE I

Compound A: 2-[N—(2-propynyl)amino]benzoxazole

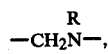

Compound B: 2-[N—(2-propynyl)amino]benzothiazole

Compound C: 2-[N—(2-propynyl)aminomethyl]benzothiazole

Compound D: 2-[N—methyl-N—(2-propynyl)amino]-benzoxazole

Compound E: 2-[N—(2-propynyl)amino]benzoselenazole

Compound F: 1-methyl-2-[N,N—(di-2-propynyl)amino]-benzimidazole

Compound G: 4,5-diphenyl-2-[N—(2-propynyl)amino]-oxazole

Compound H: 5-chloro-2-[N—(2-propynyl)amino]-benzoxazole

TABLE I-continued

| | |
|---|---|
| Compound I | 6-ethyl-2-[N—(2-propynyl)amino]-benzoxazole (structure: 5-chloro-benzoxazole with NHCH₂C≡CH) |
| | 6-ethyl-benzoxazole with NHCH₂C≡CH |
| Compound J | 2-[N—(2-butynyl)amino]benzoxazole (benzoxazole with NHCH₂C≡C—CH₃) |
| Compound K | 2-[N—(2-butynyl)amino]benzothiazole (benzothiazole with NHCH₂C≡C—CH₃) |
| Compound L | 2-(N—(2-butynyl)aminomethyl]benzothiazole (benzothiazole with CH₂NHCH₂C≡CCH₃) |
| Compound N | 2-[N—methyl-N—(2-butynyl)amino]-benzoxazole (benzoxazole with N(CH₃)—CH₂C≡C—CH₃) |
| Compound O | 2-[N—(2-butynyl)amino]benzoselenazole (benzoselenazole with NHCH₂C≡C—CH₃) |

The silver halide emulsions employed in the present invention can be any of the silver halide emulsions known in the art which are desirably protected against latent image fading. The silver halide emulsions can be comprised of silver bromide, silver chloride, silver chlorobromide, silver chloroiodide, silver bromoiodide, silver chlorobromoiodide or mixtures thereof. The emulsions can include coarse, medium or fine grain silver halide grains and can be monodisperse or polydisperse.

The silver halide emulsions are preferably surface latent image-forming emulsions. They can be chemically sensitized with active gelatin, as illustrated by T. H. James, *The Theory of the Photographic Process*, 4th Ed., Macmillan, 1977, pp. 67-76, or with sulfur, selenium, tellurium, gold, platinum, palladium, iridium, osmium, rhenium or phosphorus sensitizers or combinations of these sensitizers, such as at pAg levels of from 5 to 10, pH levels of from 5 to 8 and temperatures of from 30° to 80° C., as illustrated by *Research Disclosure*, Vol. 134, June 1975, Item 13452, Sheppard et al U.S. Pat. No. 1,623,499, Matthies et al U.S. Pat. No. 1,673,522, Waller et al U.S. Pat. No. 2,399,083, Damschroder et al U.S. Pat. No. 2,642,361, McVeigh U.S. Pat. No. 3,297,447, Dunn U.S. Pat. No. 3,297,446, McBride U.K. Pat. No. 1,315,755, Berry et al U.S. Pat. No. 3,772,031, Gilman et al U.S. Pat. No. 3,761,267, Ohi et al U.S. Pat. No. 3,857,711, Klinger et al U.S. Pat. No. 3,565,633, Oftedahl U.S. Pat. Nos. 3,901,714 and 3,904,415 and Simons U.K. Pat. No. 1,396,696; chemical sensitization being optionally conducted in the presence of thiocyanate derivatives, as described in Neitz et al U.S. Pat. No. 2,222,264, Damschroder U.S. Pat. No. 2,642,361; thioether compounds, as disclosed in Lowe et al U.S. Pat. No. 2,521,926, Williams et al U.S. Pat. No. 3,021,215 and Bigelow U.S. Pat. No. 4,054,457 and azaindenes, azapyridazines and azapyrimidines, as described in Dostes U.S. Pat. No. 3,411,914, Kuwabara et al U.S. Pat. No. 3,554,757, Oguchi et al U.S. Pat. No. 3,565,631 and Oftedahl U.S. Pat. No. 3,901,714. Additionally or alternatively, the emulsions can be reduction sensitized e.g., with hydrogen, as illustrated by Janusonis U.S. Pat. No. 3,891,446 and Babcock et al U.S. Pat. No. 3,984,249, by low pAg (e.g., less than 5) high pH (e.g., greater than 8) treatment or through the use of reducing agents, such as stannous chloride, thiourea dioxide, polyamines and amineboranes, as illustrated by Allen et al U.S. Pat. No. 2,983,609, Oftedahl et al *Research Disclosure*, Vol. 136, Aug. 1975, Item 13654, Lowe et al U.S. Pat. Nos. 2,518,696 and 2,739,060, Roberts et al U.S. Pat. Nos. 2,743,182 and '183, Chambers et al U.S. Pat. No. 3,026,203 and Bigelow et al U.S. Pat. No. 3,361,564. (*Research Disclosure* is published by Industrial Opportunities Ltd., Homewell, Havant Hampshire, PO9 1EF, United Kingdom.)

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls and streptocyanines. Particularly useful dyes are benzoxazole, benzimidazole and benzothiazole carbocyanine dyes.

The photographic silver halide emulsions can contain various colloids alone or in combination as vehicles. Suitable hydrophilic material include both naturally occurring substances such as proteins, protein derivatives, cellulose derivatives e.g., cellulose esters, gelatin e.g., alkali-treated gelatin (cattle, bone or hide gelatin) or acid-treated gelatin (pigskin gelatin), gelatin derivatives e.g., acetylated gelatin, phthalated gelatin and the like, polysaccharides such as dextran, gum arabic, zein, casein, pectin, collagen derivatives, collodion, agar-agar, arrowroot, albumin and the like. The vehicles can be hardened by conventional procedures. Further details of the vehicles and hardeners are provided in *Research Disclosure*, December 1978, Item 17643, Sections IX and X.

The 2-propynylamino or 2-butynylamino substituted heterocycle can be added to the silver halide emulsion at any point subsequent to precipitation of the silver halide grains so that it will interact with the silver halide grains prior to exposure of the emulsion. Preferably, the 2-propynylamino or 2-butynylamino substituted heterocycle is added to the emulsion after chemical and spectral sensitization, but prior to coating. However, it can be present during these sensitization processes.

The optimum amount of 2-propynylamino or 2-butynylamino substituted heterocycle added to the emulsion will depend upon such factors as the particular 2-propynylamino or 2-butynylamino substituted heterocycle, the particular silver halide emulsion, the location of latent image formation, the nature of other components of the emulsion, and the like. Useful amounts are generally within the range 0.002 to 10 millimoles of 2-propynylamino or 2-butynylamino substituted heterocycle per mole of silver. Preferably, the 2-propynylamino or 2-butynylamino substituted heterocycle compound is incorporated in the emulsion in an amount of 0.02 to 0.5 millimole per mole of silver.

The photographic silver halide emulsions of this invention and photographic elements employing them can contain other addenda conventional in the photographic art. Useful addenda are described, for example, in *Research Disclosure*, December 1978, Item 17643. Useful addenda include spectral sensitizing dyes and desensitizers, antifoggants, couplers (such as dye forming couplers, masking couplers and DIR couplers) DIR compounds, anti-stain agents, image dye stabilizers, absorbing materials such as filter dyes and UV absorbers, light scattering materials, coating aids, plasticizers and lubricants, and the like.

The photographic elements of the present invention can be simple black-and-white or monochrome elements comprising a support bearing a layer of the silver halide emulsion, or they can be multilayer and/or multicolor elements. They can be designed for processing with separate solution or for in-camera processing. Multicolor elements contain dye image forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion or emulsions can be disposed as one or more segmented layers, e.g., as by the use of microvessels or microcells, as described in Whitmore U.S. Pat. No. 4,362,806.

A preferred color photographic element according to this invention comprises a support bearing at least one blue-sensitive silver halide emulsion layer having associated therewith a yellow dye-forming coupler, at least one green-sensitive silver halide emulsion layer having associated therewith a magenta dye-forming coupler and at least one red-sensitive silver halide emulsion layer having associated therewith a cyan dye-forming coupler, at least one of the silver halide emulsion layers containing a latent image stabilizing compound of this invention. In accordance with a particularly preferred aspect of the present invention, the 2-propynylamino or 2-butynylamino substituted heterocycle is contained in a yellow dye-forming blue-sensitive silver halide emulsion.

The elements of the present invention can contain additional layers conventional in photographic elements, such as overcoat layers, spacer layers, filter layers, antihalation layers, scavenger layers and the like. The support can be any suitable support used with photographic elements. Typical supports include polymeric films, paper (including polymer-coated paper), glass and the like. Details regarding supports and other layers of the photographic elements of this invention are contained in *Research Disclosure*, December 1978, Item 17643, referred to above, the disclosure of which is incorporated herein by reference.

The following examples further illustrate this invention.

EXAMPLE 1

Preparation of Compound A 2-propynylamine (0.02 mole) was added slowly to a reaction vessel containing 2-chlorobenzoxazole (0.01 mole) at $-10°$ C. in a dry ice acetone bath. After the addition was completed, the mixture was stirred at $0°$ C. for one hour, placed in a refrigerator for approximately 15 hours and then treated with dry ether. The resulting solid was removed by filtration; and the filtrate was concentrated to a residue which was extracted with hot high boiling ligroin. The ligroin extracts were concentrated and cooled to yield a creamy solid; yielding (64%).

Anal. Calcd.: C, 69.8; H, 4.7; N, 16.3, Anal. Found: C, 69.3; H, 4.3; N, 16.2.

EXAMPLE 2

Preparation of Compound B 2-propynylamine (0.01 mole) was added to a reaction vessel containing 2-chlorobenzothiazole at $100°$ C. The reaction mixture was maintained at $100°$ C. for approximately 15 hours, cooled, treated with acetone, and filtered to remove a solid. The filtrate was concentrated to a solid residue which was subjected to extraction with hot low boiling ligroin. The ligroin extracts were concentrated and filtered to yield a pale yellow solid; yield 170 mg (9%).

Anal. Calcd.: C, 63.8; H, 4.3; N, 14.9, Anal. Found: C, 63.7; H, 4.5; N, 14.7.

EXAMPLE 3

Preparation of Compound C 2-propynylamine (0.018 mole) was combined with 2-chloromethylbenzothiazole (0.010 mole) and 30 ml of acetonitrile in a reaction vessel and heated at $80°$ C. for 4 hours. The mixture was cooled, combined with dichloromethane and washed with aqueous potassium carbonate solution. The organic phase was separated, dried, and concentrated and cooled. The solid was collected by filtration, washed with ligroin and then recrystallized from ligroin; yield 0.8 g (40%), m.p. $77°-78.5°$ C.

Anal. Calcd.: C, 65.3; H, 5.0; N, 13.8, Anal. Found: C, 65.2; H, 4.7; N, 14.0.

EXAMPLE 4

Preparation of Compound D

2-Chlorobenzoxazole (0.01 mole) was added with stirring to a reaction vessel containing N-methyl-2-propynylamine (0.02 mole) at $-10°$ C. After 10 minutes, a white solid appeared and stirring was discontinued. The reaction mixture was allowed to come to room temperature. After 1 hour, the mixture was treated with acetone and filtered. The filtrate was concentrated to a solid which was recrystallized from hot ligroin; yield 0.7 g (37.6%).

Anal. Calcd.: C, 70.95; H, 5.41; N, 15.04, Anal. Found: C, 71.2; H, 5.5; N, 14.9.

EXAMPLE 5

Preparation of Compound E 2-propynylamine (0.036 mole) was added to a reaction vessel containing 2-chlorobenzoselenazole (0.0136 mole) at ice bath temperature. The mixture was allowed to stir at room temperature for approximately 2½ days. Acetone was added to the reaction mixture to obtain a precipitate. The filtrate was concentrated to obtain a brown residue which was heated in ligroin and cooled. The golden/beige crystals were collected by filtration and recrystallized from ligroin; yielding 1.1 g (34.4%).

Anal. Calcd.: C, 51.06; H, 3.4; N, 11.9, Anal. Found: C, 51.3; H, 3.4; N, 12.1.

EXAMPLE 6

Preparation of Compound J

Pyridine (0.6 g, 1 eq.) was added slowly to a solution of 2-chlorobenzoxazole (1.1 g, 7.2 mmole) in acetonitrile (50 mol) which had been cooled in an ice bath. 2-Butynylamine (0.5 g, 7.2 mmole) was added next while allowing the reaction mixture to come to room temperature. After stirring for 30 minutes triethylamine (1 eq.) was added; the mixture was refluxed for 1 hour and then allowed to stand for approximately 15 hours. After adding dichloromethane (150 ml) and extracting with a saturated sodium chloride solution, the organic layer was dried and evaporated to a solid. The dried solid was triturated with hexane. A white solid crystallized from the hexane; yield 300 mg (23%), m.p. 93°–95C° C.

Anal. Calcd.: C, 71.0; H, 5.4; N, 15.0, Found: C, 70.8; H, 5.6; N, 14.7.

EXAMPLE 7

(A Comparative Example)

This is a control coating. No latent image stabilizer is present. A multilayer incorporated coupler material such as described by Eeles and O'Neill in U.K. Pat. No. 1,500,497 (1978), page 4, color film 2 was coated as follows:

---

Layer 11 - Overcoat layer
  Gelatin (0.61 g/m²) overcoat
Layer 10 - UV Absorbing layer
  Gelatin (0.61 g/m²) + UV absorber (0.34 g/m²) + antistain agent (0.07 g/m²)
Layer 9 - Faster Yellow dye forming emulsion layer - 0.80 μm sulfur + gold sensitized AgBr emulsion (1.62 g Ag/m²) + gelatin (1.72 g/m²) + yellow dye forming coupler (0.33 g/m²)
Layer 8 - Slower yellow dye forming emulsion layer 0.80 μm sulfur + gold sensitized AgBr emulsion (0.78 g Ag/m²) + gelatin (1.25 g/m²) + yellow dye forming coupler (0.86 g/m²)
Layers 1–7 - See U.K. Patent 1,500,497

---

Film Support
UV Absorber: α-[3-α-(2,4-di-tert-amylphenoxy)butyramidbenzoyl]-2-methoxyacetanilide
Antistain Agent: Didodecylhydroquinone
Yellow Coupler:

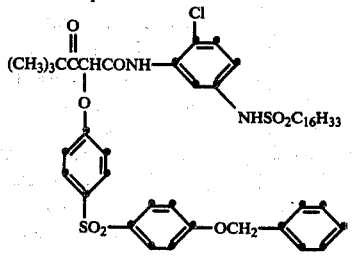

Samples of the coating were subjected to the following storage, exposure and processing variations:
Sample A Exposed and processed immediately
Sample B Stored 2 weeks/25.6° C./50% relative humidity, exposed, and processed
Sample C Exposed, stored 2 weeks/25.6° C./50% relative humidity, and processed Table II contains the sensitometric results.

EXAMPLE 8

Example 8 was identical to Comparative Example 7, except that the faster yellow dye forming emulsion layer (Layer 9) contained Compound A (0.20 mmole/mole Ag). Samples were subjected to the same storage, exposure, and processing variations as described in Comparative Example 7. Table II contains the sensitometric results.

TABLE II

| | | Relative Blue Speeds Storage Condition | | | |
|---|---|---|---|---|---|
| Example | Compound | A | B | C | Comments |
| 7 | None | 100 | 95 | 83 | Control |
| 8 | A | 129 | 123 | 170 | Invention |

Exposure: 1/50 second, 5500° C.
Process: 3¼ min Kodak Flexicolor Process
(British Journal Photography, July 1974, 579–589).

Relative speeds were obtained at 0.2 above $D_{min}$. The above speed and latent image stability was obtained with a minimal increase in $D_{min}$ (+0.02) in comparison to the control coating.

EXAMPLE 9

Example 9 was the same as Example 8, except Compound B was coated in place of Compound A at 0.1 millimole/mole Ag. A control coating identical to Example 9, except for the absence of Compound B was also prepared.

Samples of both the control and the example coatings were exposed and subjected to the same storage and processing conditions as described in Examples 7 and 8. The sensitometric results were as follows:

TABLE III

| | | Relative Blue Speeds Storage Condition | | |
|---|---|---|---|---|
| Example | Control | A | B | C |
| Control | None | 100 | 100 | 59 |
| 9 | B | 159 | 145 | 170 |

In addition to Compounds A and B, similar results were obtained with Compounds C, D and E.

EXAMPLE 10

A series of photographic silver halide coatings were prepared as follows:

A nonspectrally sensitized, sulfur and gold sensitized, 0.8 μm silver bromide emulsion at a pH of approximately 5.0 and pAg of 9.0 was prepared. To individual portions of the emulsion were added compounds as indicated in the Table IV which follows. The individual emulsions were then coated on a cellulose acetate film suport at a coverage of 5.81 grams silver per square meter and 13.2 grams gelatin per square meter. After drying, individual portions of each of the coatings were tested using three different procedures as follows:

A. Exposed through a step tablet for 1/50 second to a 500 watt, 5500° K. tungsten light and immediately processed for 6 minutes in a p-methylaminophenol sulfate/hydroquinone developer, fixed, washed, and dried.
B. Stored for one week at 48.9° C. and 50% relative humidity and then exposed and processed as in (A).
C. Exposed as in (A), stored for one week as in (B) and then processed as in (A).

The relative speeds obtained with the coatings using each of the three procedures are shown in Table IV which follows. Procedure (C) shows the effect of latent image fading relative to both procedures (A) and (B). The greater the loss of relative speed, the greater the amount of latent image fading.

TABLE IV

| Coating | Compound | Amount millimoles/mole Ag | Relative Speeds A | B | C |
|---|---|---|---|---|---|
| Control 1 | None | — | 100 | 257 | 45 |
| Example | A | 0.20 | 100 | 195 | 65 |
| Example | A | 1.00 | 97 | 178 | 85 |
| Example | A | 3.00 | 78 | 141 | 95 |
| Control 2 | Y | 0.20 | 17.2 | 55 | * |
| Control 3 | Y | 1.00 | 17.2 | 67 | * |
| Control 4 | Y | 3.00 | 14.0 | 69 | * |

*= Gross desensitization

Compound Y = 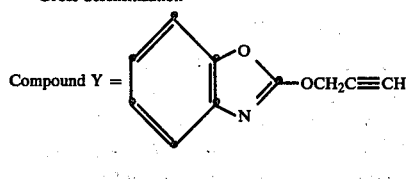

EXAMPLES 11 THROUGH 14

Generally similar testing procedures were employed as those set forth in Examples 7 and 8. The results are summarized below in Table V.

TABLE V

| Coating | Compound | Amount millimoles/mole Ag | Relative Speeds A | B | C |
|---|---|---|---|---|---|
| Control 5 | None | — | 100 | 105 | 97 |
| Example 11 | A | 0.10 | 145 | 138 | 214 |
| Example 12 | F | 0.15 | 148 | 155 | 186 |
| Example 13 | G | 0.15 | 138 | 135 | 186 |
| Example 14 | J | 0.10 | 138 | 126 | 186 |

In each instance the incorporation of a 2-propynylamino or 2-butynylamino substituted heterocycle resulted in overcoming a loss of speed on storage that was observed in its absence.

This invention has been described in detail with reference to preferred embodiments thereof but it will be understood that variations and modifications can be effected within the spirit and scope of the invention.

What is claimed is:

1. A photographic silver halide emulsion containing a photographically effective amount of a compound represented by the formula

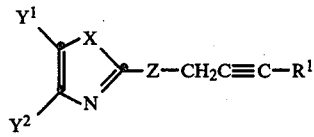

wherein:
X is —O—, —S—, —Se—, or

$Y^1$ and $Y^2$ individually represent hydrogen or an aromatic nucleus or together represent the atoms completing a fused aromatic nucleus;
Z is

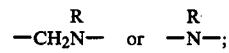

R is hydrogen or lower alkyl of from 1 to 5 carbon atoms; and
$R^1$ is hydrogen or methyl, provided that $Y^1$ and $Y^2$ individually represent hydrogen or an aromatic nucleus when $R^1$ is hydrogen.

2. A photographic silver halide emulsion according to claim 1 wherein X, $Y^1$ and $Y^2$ complete a benzoxazole nucleus.

3. A photographic silver halide emulsion according to claim 1 wherein X, $Y^1$ and $Y^2$ complete a benzothiazole nucleus.

4. A photographic silver halide emulsion according to claim 1 wherein X, $Y^1$ and $Y^2$ complete a benzoselenazole nucleus.

5. A photographic silver halide emulsion according to claim 1 wherein X, $Y^1$ and $Y^2$ complete a benzimidazole nucleus.

6. A photographic silver halide emulsion according to claim 1 wherein R is hydrogen or methyl.

7. A photographic silver halide emulsion according to claim 1 wherein said compound is present in a concentration sufficient to increase photographic speed.

8. A photographic silver halide emulsion according to claim 1 wherein said compound is present in a concentration sufficient to reduce latent image fading.

9. A photographic silver halide emulsion according to claim 1 wherein said compound is present in a concentration of from 0.002 to 10 millimoles per silver mole.

10. A photographic element comprised of a support and, located thereon, at least one layer comprised of a photographic silver halide emulsion according to claim 1, 2, 3, 4, 5, 6, 7, 8, or 9.

11. In a color photographic element comprising a support bearing at least one blue-sensitive silver halide emulsion layer having associated therewith a yellow dye-forming coupler, at least one green-sensitive silver halide emulsion layer having associated therewith a magenta dye-forming coupler, and at least one red-sensitive silver halide emulsion layer having associated therewith a cyan dye-forming coupler, the improvement wherein at least one of the silver halide emulsion layers contains a latent image stabilizing amount of a compound represented by the formula:

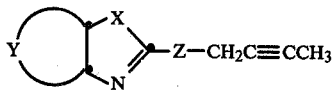

wherein:
X and Y complete a heterocyclic nucleus chosen from the class consisting of benzoxazole, benzothiazole, benzoselenazole, and benzimidazole;
Z is

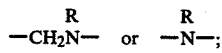

and
R is hydrogen or lower alkyl.

12. A color photographic element according to claim 11 in which R is hydrogen or methyl.

13. A color photographic element according to claim 11 in which said compound is present in a concentration of from 0.02 to 0.3 millimole per silver mole.

14. A color photographic element according to claim 11 wherein said compound is contained in a blue-sensitive silver halide emulsion layer.

15. A process comprising incorporating in a photographic silver halide emulsion in a photographically effective amount a compound represented by the formula

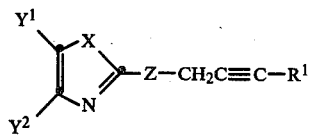

wherein:
X is oxygen, sulfur, selenium, or nitrogen;
$Y^1$ and $Y^2$ individually represent hydrogen or an aromatic nucleus or together represent the atoms necessary to complete a fused aromatic nucleus;
Z is

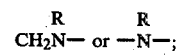

R is hydrogen or lower alkyl of from 1 to 5 carbon atoms; and
$R^1$ is hydrogen or methyl, provided that $Y^1$ and $Y^2$ individually represent hydrogen or an aromatic nucleus when $R^1$ is hydrogen.

16. A process according to claim 15 wherein said compound is incorporated in an amount sufficient to both (a) stabilize said emulsion against latent image fading between imagewise exposure and development of a visible image and (b) increases the sensitivity of said emulsion.

* * * * *